United States Patent [19]

Schündehütte et al.

[11] Patent Number: 5,051,507
[45] Date of Patent: Sep. 24, 1991

[54] PROCESS FOR THE PREPARATION OF 4,5,6-TRICHLOROPYRIMIDINE

[75] Inventors: Karl-Heinz Schündehütte; Gunther Beck, both of Leverkusen; Kurt Findeisen, Odenthal; Hermann Henk, Colonge, all of Fed. Rep. of Germany

[73] Assignee: Bayer Aktiengesellschaft, Leverkusen, Fed. Rep. of Germany

[21] Appl. No.: 463,648

[22] Filed: Jan. 11, 1990

[30] Foreign Application Priority Data

Jan. 13, 1989 [DE] Fed. Rep. of Germany ....... 3900917

[51] Int. Cl.$^5$ ............................................ C07D 239/30
[52] U.S. Cl. .................................................... 544/334
[58] Field of Search ......................................... 544/334

[56] References Cited

U.S. PATENT DOCUMENTS 3,509,032  4/1970  Beck et al. .......................... 544/334
3,920,649  11/1975 Beck et al. .......................... 260/251

FOREIGN PATENT DOCUMENTS 0249257 12/1987 European Pat. Off. .
1545313  9/1968 France .

Primary Examiner—John M. Ford
Attorney, Agent, or Firm—Sprung Horn Kramer & Woods

[57] ABSTRACT

New process for the preparation of 4,5,6-trichloropyrimidine, characterized in that a protonated dialkylaminopropionitrile of the general formula I

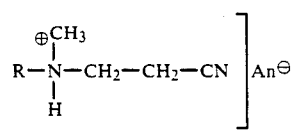

in which R is $C_1$–$C_4$-alkyl and an$^-$ is an anion is treated with chlorine in an inert solvent in the presence of organic catalysts or $PCl_3$ or $PCl_5$.

3 Claims, No Drawings

PROCESS FOR THE PREPARATION OF 4,5,6-TRICHLOROPYRIMIDINE

The present invention relates to a new process for the preparation of 4,5,6-trichloropyrimidine, characterized in that a protonated dialkylaminopropionitrile of the general formula I

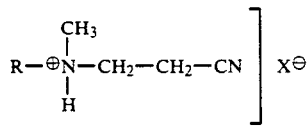

in which R denotes a hydrogen atom or an alkyl radical having 1 to 4 C atoms and $X^-$ represents an anion, is treated with chlorine, preferably at about 100° to 150° C., in a solvent which is inert to the reaction in the presence of organic catalysts or $PCl_3$ or $PCl_5$.

Preferred solvents are those which are stable to chlorine under the reaction conditions, for example chlorinated, aliphatic and aromatic hydrocarbons, such as chloroform or carbon tetrachloride, but particularly chlorobenzene and dichlorobenzene and also phosphorus oxychloride and isododecane.

Further suitable solvents are chloropyrimidines, in particular 4,5,6-trichloropyrimidine.

Phosphorus oxychloride is a particularly preferred solvent.

Suitable anions are particularly anions of inorganic strong acids, such as hydrochloric acid or sulphuric acid. In addition, anions of organic acids are also suitable.

Examples of suitable organic catalysts are openchain or cyclic carboxamides, such as $C_1$–$C_{12}$-dialkylformamides, in particular dimethylformamide, dibutylformamide, methyldodecylformamide, N-$C_1$-$C_{12}$-alkylpyrrolidones, such as N-methylpyrrolid-2-one, N-$C_1$-$C_{12}$-alkylcaprolactams, such as N-methylcaprolactam, and also trialkylphosphites, triarylphosphites and triarylphosphine oxides (aryl preferably denoting optionally substituted phenyls).

The catalysts can also be employed as a mixture with one another, preferably in amounts from 0.1 to 30, preferably 10 to 20, % by weight, relative to I.

It is preferable to carry out the reaction in such a way that the dialkylaminopropionitrile is put into the previously taken solvent and is then protonated by adding about 1.1 to 1.3 moles of acid. In the course of this the mixture heats up and the ammonium compound is generally precipitated as a white, crystalline salt. 10 to 20% by weight of the catalyst are then added and the suspension is heated to about 120° to 130° C. Chlorine is then passed in smoothly at this temperature until the reaction is complete. The total time—depending on the catalyst—is about 5 to 20 hours. The reaction mixture is then in the form of a solution of yellowish colour. 400 to 600 g of chlorine are required for the reaction per mole of free starting amine.

The mixture can then be separated by distillation. The reaction product consists of virtually pure 4,5,6-trichloropyrimidine, which can in some cases contain small amounts of tetrachloropyrimidine as an impurity; this can also be removed by fractional distillation.

In comparison with previously known processes (for example U.S. Pat. No. 3,509,032) the synthesis according to this invention has the advantage of being more cost-efficient and, at the same time, of greater purity of the resulting product.

4,5,6-Trichloropyrimidine is an interesting precursor for the reactive component 4,6-difluoro-5-chloropyrimidine (see Offenlegungsschrift 1,644,203).

EXAMPLE 1

98 g of 3-dimethylaminopropionitrile are dissolved in 600 ml of phosphorus oxychloride and the hydrochloride of 3-dimethylaminopropionitrile is formed by passing in 40 g of hydrogen chloride (over a period of about 15 minutes). 15 g of phosphorus pentachloride are introduced into this suspension, the mixture is heated to boiling point (106° C.) and chlorine is passed in (about 45 to 50 g per hour) under UV radiation. After 10 hours a clear pale yellow solution forms and no more chlorine is absorbed. The total amount of chlorine passed in is 465 g. At the end of the chlorination the system is flushed with nitrogen for 30 minutes, after which the phosphorus oxychloride is distilled off and the residue is distilled in a water jet vacuum at 87° to 125° C. 178 g of a distillate is obtained which consists of 90.2% of 4,5,6-trichloropyrimidine and 9.1% of 2,4,5,6-tetrachloropyrimidine.

If the same procedure is followed as that described above but the following compounds are used as catalysts:

2. dimethylformamide
3. dibutylformamide
4. N-methylpyrrolidone
5. N-methylcaprolactam
6. trialkyl phosphite
7. triphenyl phosphite
8. triphenylphosphine
9. triphenylphosphine oxide
10. phosphorus pentachloride similar amounts of 4,5,6-trichloropyrimidine are obtained after comparable reaction times.

EXAMPLE 2

198 g (2 mol) of dimethylaminopropionitrile and 1,105 g of chlorobenzene are initially placed in a 2 l four-necked flask equipped with a stirrer, a gas inlet tube, a thermometer and an upright condenser, 95 g (2.6 mol) of hydrogen chloride gas are first passed in. In the course of this the temperature rises from 20° C. to 90° C., and the hydrochloride is precipitated in the form of white crystals, 10 g of triphenylphosphine and 20 g of phosphorus pentachloride are then added to this suspension and a total of 880 g of anhydrous chlorine is passed in at a uniform rate at approx. 125° C. within 10 hours. The gas stream evolved contains a little $Cl_2$, chloroform and carbon tetrachloride, as well as HCl. When the chlorination is complete, the system is flushed with nitrogen for 30 minutes and the reaction mixture is then subjected to fractional distillation. After the chlorobenzene has been removed, 339 g of 4,5,6-trichloropyrimidine pass over at b.p. 90°–95° C./14 mb. The melting point is 51°–51° C. from petroleum ether. Yield: 92.5%.

If the procedure is as indicated in this example and the following compounds are used as catalysts:

2. dimethylformamide
3. dibutylformamide
4. N-methylpyrrolidone

5. N-methylcaprolactam 6. trialkyl phosphite 7. triphenyl phosphite 8. triphenylphosphine 9. triphenylphosphine oxide 10. phosphorus pentachloride similar amounts of 4,5,6-trichloropyrimidine are obtained after comparable reaction times.

The synthesis can also be carried out analogously in o-dichlorobenzene.

We claim:

1. Process for the preparation of 4,5,6-trichloropyrimidine, characterized in that a protonated dialkylaminopropionitrile of formula

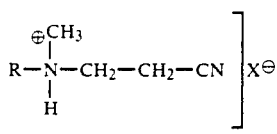

wherein
 R is H or $C_1$–$C_4$-alkyl and
 $X^{\ominus}$ is an anion
is treated with chlorine in the presence of organic catalysts selected from:
 open chain or cyclic carboxamides,
 N-$C_1$-$C_{12}$-alkylpyrrolidones,
 N-$C_1$-$C_{12}$-alkylcaprolactams,
 trialkylphosphites,
 triarylphosphites,
 triarylphosphine oxides and
 triphenylphosphine
 or $PCl_5$ or $PCl_3$
 or mixtures of these catalyst compounds
and in the presence of phosphorus oxychloride as a solvent.

2. Process according to claim 1, characterized in that chlorination is carried out at approx. 100° to 150° C.

3. Process according to claim 1, characterized in that 400 to 600 g of chlorine are used per mole of dialkylaminopropionitrile.

* * * * *